United States Patent [19]

Kurka et al.

[11] Patent Number: 4,879,290
[45] Date of Patent: Nov. 7, 1989

[54] AGENTS FOR THE PREVENTION OF RANKING FIGHTS IN PIGS

[75] Inventors: Peter Kurka, Hilden; Leppold Goetze, Wuppertal, both of Fed. Rep. of Germany

[73] Assignee: Bayer Aktiengesellschaft, Leverkusen, Fed. Rep. of Germany

[21] Appl. No.: 203,039

[22] Filed: Jun. 6, 1988

[30] Foreign Application Priority Data

Jun. 16, 1987 [DE] Fed. Rep. of Germany ....... 3720074

[51] Int. Cl.$^4$ ...................... A61K 31/54; A61K 31/50
[52] U.S. Cl. .................................. 514/223.2; 514/253
[58] Field of Search ............................. 514/223.2, 253

[56] References Cited

PUBLICATIONS

Chemical Abstracts, vol. 102, 1985, 220896m.
Blodinger–Formulation of Veterinary Dosage Forms Marcel Dekker, Inc., N.Y. and Basel, pp. 176–180.

Primary Examiner—Frederick E. Waddell
Attorney, Agent, or Firm—Sprung Horn Kramer & Woods

[57] ABSTRACT

A method of suppressing ranking fights during assembly of groups of pigs which comprises administering to such pigs an amount effective therefor of a 2-pyrimidinyl-1-piperazine derivative of the formula (I)

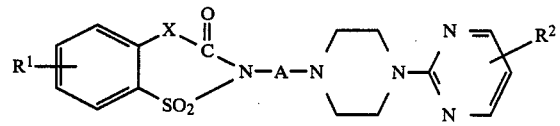

in which
$R^1$ and $R^2$ each independently represents at least one radical selected from the groups consisting of hydrogen, $C_{1-4}$-alkyl, halogen, hydroxyl, nitro, $C_{2-4}$-alkenyl, $C_{1-4}$-alkoxy, $C_{1-4}$-alkylthio, $C_{1-4}$-halogenoalkyl, $C_{1-4}$-halogenoalkoxy and $C_{1-4}$-halogenoalkylmercapto,
X is a direct bond or a radical $N-R^3$,
$R^3$ is hydrogen or $C_{1-4}$-alkyl, and
A is an optionally substituted alkylene radical with up to 6 C atoms,
or a physiologically acceptable salt thereof.

6 Claims, No Drawings

AGENTS FOR THE PREVENTION OF RANKING FIGHTS IN PIGS

The present invention relates to agents for the prevention of ranking fights in pigs and also to their preparation and use.

For the suppression of ranking fights during regrouping, i.e. during assembly of new groups (transports, transfer measures), pharmaceuticals must be employed in the pig which hpossess a calming action on the intragroup aggression in order to avoid partial or total losses. At present, neuroleptics are predominantly used for this indication (phenothiazine derivatives or butyrophenone derivatives), but a corresponding activity has also been detected for benzodiazepine derivatives (diazepam). Disadvantages of the former consist in the influencing of autonomic functions (respiratory depression, hypothermia, hypotension) and also, particularly in the pig, in the appearance of paradoxical reactions, whereas the disadvantages of the benzodiazepines are to be seen in the more or less pronounced muscle relaxation, amnesia and additionally in the appearance of paradoxical reactions. Moreover, the sedation of the pigs which occurs in the action profile of both classes of substance can lead to a normal or increased fighting activity during or after the decline in the effective blood levels, since the animals are only then in a position to become familiar with each other and to bring about a rank ordering.

Pharmacological test models in laboratory animals (for example, Tedeschi fighting mouse test, inhibition of the territorial aggressiveness of the rat) are selection criteria for compounds which can be employed for the abovementioned indication. However, no reliable conclusion can be drawn from these tests regarding the suitability of compounds for the suppression of ranking fights in pigs. On the one hand, paradoxical reactions can appear, particularly in pigs, so that the reverse effect, namely an increase of ranking fights, is the result. If the sedative component in the action profile is too strong, the same disadvantageous action can make use impossible.

Further side effects or undesired actions (interference with autonomic functions, distinct myorelaxation) can have an adverse effect, particularly during transport of the animals.

It has now been found that 2-pyrimidinyl-1-piperazine derivatives of the formula (I)

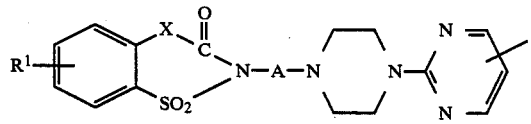

in which
R$^1$ and R$^2$ each independently represents at least one radical selected from the groups consisting of hydrogen, C$_{1}$-C$_4$-alkyl, halogen, hydroxyl, nitro, C$_{2-4}$-alkenyl, C$_{1-4}$-alkoxy, C$_{1-4}$-alkylthio, C$_{1-4}$-halogenoalkyl, C$_{1-4}$-halogenoalkoxy and C$_{1-4}$-halogenoalkylmercapto,
X represents a direct bond or a radical

R$^3$ represents hydrogen or C$_{1-4}$-alkyl, and
A represents a straight-chain or branched alkylene radical with up to 6 C atoms which can be optionally substituted,
and also their physiologically acceptable salts with acids, are outstandingly suitable for the suppression of ranking fights during assembly of groups of pigs.

The compounds of the formula (I) and their preparation are disclosed in EP-OS (European Published Specification) 129,128.

Preferred compounds of the formula (I) are those in which
R$^1$ represents hydrogen, halogen, in particular chlorine or fluorine, methyl, ethyl, methoxy, ethoxy, methylenedioxy or ethylenedioxy;
R$^2$ represents hydrogen or halogen, in particular chlorine or fluorine,
X represents a direct bond or the radical

R$^3$ represents hydrogen or C$_{1-4}$-alkyl, in particular methyl or ethyl, and
A represents a straight-chain alkylene radical with 3 to 6 C atoms, in particular n-propylene or n-butylene.

Particularly preferred compounds of the formula (I) are those in which
R$^1$ represents hydrogen, fluorine, chlorine or methoxy,
R$^2$ represents hydrogen or fluorine,
X represents a direct bond or a radical

A represents (CH$_2$)$_3$ or (CH$_2$)$_4$.

The following compounds may be mentioned individually:

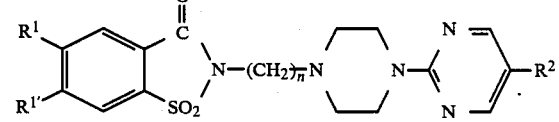

| R$^1$ | R$^3$ | n |
|---|---|---|
| H | H | 3 |
| H | CH$_3$ | 3 |
| H | H | 4 |
| H | CH$_3$ | 4 |
| Cl | H | 3 |
| Cl | CH$_3$ | 3 |
| OCH$_3$ | H | 3 |
| OCH$_3$ | CH$_3$ | 3 |

-continued

| R¹ | R¹' | R² | n |
|----|-----|----|----|
| Cl | H | H | 4 |
| H | Cl | H | 4 |
| F | H | H | 4 |
| F | H | H | 3 |
| H | H | H | 3 |
| H | H | H | 4 |
| H | H | F | 4 |

2-(4-(4-(2-Pyrimidinyl)-1-piperazinyl-propyl-1,2-benzisothiazol-3(2H)one-1,1-dioxide and 2-(4-(4-pyrimidinyl)-1-piperazinyl-1,2-benzisothiazol-3(2H)one-1, 1-dioxide (ipsapirone) may be particularly emphasized.

Inorganic and organic acids may be mentioned as acids with which the compounds of the formula (I) can form salts. The inorganic acids include hydrochloric acid, sulphuric acid and phosphoric acid. The organic acids include formic acid and acetic acid.

The active compounds are used in the form of preparations suitable for animals.

Preparations suitable for animals are:

Solutions such as injection solutions, oral solutions, concentrates for oral administration after dilution, solutions for use on the skin or in body cavities, infusion formulations and gels; emulsions and suspensions for oral or cutaneous application and also for injection; solid preparations such as powders, premixes or concentrates, granulates, pellets, tablets, boli and capsules; aerosols and inhalants.

Injection solutions are administered intravenously, intramuscularly and subcutaneously. 0.1 to 50 mg of active compound, preferably 0.2 to 10 mg of active compound, per kg of body weight of the animals are employed. The solutions contain 0.1 to 10%, preferably 0.2 to 5% of active compound.

Injection solutions are prepared by dissolving the active compound in a suitable solvent and, where necessary, adding additives such as solubilizers, acids, bases, buffer salts, antioxidants and preservatives. The solutons are filtered sterile and bottled.

Solvents which may be mentioned are: physiologically acceptable solvents such as water, alcohols such as ethanol, butanol, benzyl alcohol, glycerol, propylene glycol and polyethylene glycol, esters such as ethyl lactate, N-methyl-pyrrolidone and mixtures thereof.

Where appropriate, the active compounds can also be dissolved in physiologically acceptable vegetable or synthetic oils which are suitable for injection.

Solubilizers which may be mentioned are: solvents, which promote the solution of the active compound in the main solvent or prevent its precipitation. Examples are polyvinylpyrrolidone, polyoxyethylated castor oil and polyoxyethylated sorbitan ester.

Preservatives are: benzyl alcohol, trichlorobutanol, p-hydroxybenzoates and n-butanol.

Oral solutions are used directly. Concentrates are used orally after previous dilution to the application concentration. Oral solutions and concentrates are prepared as described above for the injection solutions, and sterile working can be dispensed with.

Solutions for use on the skin or in body cavities are dropped on, spread on, rubbed in, sprayed on or applied by bathing. These solutions are prepared as described above for the injection solutions. Thickeners can be added during preparation.

Thickeners are: inorganic thickeners such as bentonites, colloidal silica, aluminum monostearate, organic thickeners such as cellulose derivatives, polyvinyl alcohols and their copolymers, acrylates and methacrylates.

Gels are applied or spread onto the skin or introduced into body cavities. Gels are prepared by adding to solutions which have been prepared as described for the injection solutions, sufficient thickener to give a clear mass with an ointment-like consistency. The thickeners employed are the abovementioned thickeners.

Pour-on formulations are poured onto or sprayed onto limited areas of the skin, the active compound either penetrating the skin and acting systemically or distributing itself over the body surface.

Pour-on formulations are prepared by dissolving, suspending or emulsifying the active compound in suitable skin-compatible solvents or solvent mixtures. If appropriate, further auxiliaries such as colorants, resorption promotors, antioxidants, light-screens and adhesives are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethyl lactate, ethers such as alkylene glycol alkyl ethers such as dipropyleneglycol monomethyl ether, diethyleneglycol monobutyl ether, ketones such as acetone, methyl ethyl ketone, aromatic and/or aliphatic hydrocarbons, vegetable or synthetic oils, DMF, dimethylacetamide, N-methylpyrrolidone and 2,2-dimethyl-4-oxymethylene-1,3-dioxolane.

Colorants, which can be dissolved or suspended, are all colorants permitted for application to animals.

Resorption promotors are dimethyl sulphoxide (DMSO), spreading oils such as isopropyl myristate, dipropyleneglycol perlargonate, silicone oils, fatty acid esters, triglycerides and fatty alcohols.

Antioxidants are sulphites or metabisulphites such as potassium metabisulphite, ascorbic acid, butylhydroxytoluene, butylhydroxyanisole and tocopherol.

Light screens are, for example, substances from the benzophenone class or novantisolic acid.

Adhesives are, for example, cellulose derivatives, starch derivatives, polyacrylates, natural polymers such as alginates, and gelatin.

Emulsions can be applied orally, cutaneously or as injections.

Emulsions are either of the water-in-oil type or of the oil-in-water type.

They are prepared by dissolving the active compound in one phase and homogenizing this with the assistance of suitable emulisifiers and, if appropriate, further auxiliaries such as colorants, resorption promotors, preservatives, antioxidants, light screens and viscosity-increasing substances.

Hydrophobic phases (oils) which may be mentioned are: paraffin oils, silicone oils, natural vegetable oils such as sesame oil, almond oil, castor oil, synthetic triglycerides such as caprylic/capric acid diglyceride, triglyceride mixtures with vegetable fatty acids of chain length $C_{8-12}$ or other specifically selected natural fatty acids, partial glyceride mixtures of saturated or unsaturated fatty acids, also containing hydroxyl groups where appropriate, and mono- and diglycerides of the $C_8/C_{10}$ fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, diisopropyl adipate and ester mixtures related to the latter, etc.

Fatty alcohols such as isotridecyl alcohol, 2-octyldodecanol, cetylstearyl alcohol and oleyl alcohol.

Fatty acids, such as, for example, oleic acid and its mixtures.

Hydrophilic phases which may be mentioned are: water, alcohols, such as, for example, propylene glycol, glycerol, sorbitol and their mixtures.

Emulsifiers which may be mentioned are: surfactants (including emulsifiers and wetting agents), such as 1. non-ionogenic, for example polyoxyethylated castor oil, polyoxyethylated sorbitan mono-oleate, sorbitan monostearate, glycerol monostearate, polyoxyethyl stearate and alkylphenol polyglycol ethers, 2. ampholytic such as di-Na N-lauryl-β-iminodipropionate or lecithin, 3. anion-active, such as Na lauryl sulphate, fatty alcohol ether sulphates and mono/dialkylpolyglycol ether orthophosphate monoethanolamine salt, 4. cation-active such as cetyltrimethylammonium chloride.

Other auxiliaries which are suitable are: viscosity-increasing and emulsion-stabilizing substances such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silica or mixtures of the abovementioned substances.

Suspensions can be administered orally, cutaneously or as injections. They are prepared by suspending the active compound in an excipient liquid, if appropriate with the addition of further auxiliaries such as wetting agents, colorants, resorption promotors, preservatives, antioxidants and light screens.

Excipient liquids which may be mentioned are all homogeneous solvents and solvent mixtures.

Wetting agents (dispersing agents) which may be mentioned are:

surfactants (including emulsifiers and wetting agents) such as 1. anion-active, such as Na lauryl sulphate, fatty alcohol ether sulphates, mono/dialkylpolyglycol ether orthophosphate monoethanolamine salt, lignin sulphonates or dioctyl sulphosuccinate, 2. cation-active such as cetyltrimethylammonium chloride, 3. ampholytic such as di-Na N-lauryl-β-iminodipropionate or lecithin 4. non-ionogenic, for example polyoxyethylated castor oil, polyoxyethylated sorbitan mono-oleate, sorbitan monostearate, ethyl alcohol, glycerol monostearate, polyoxyethylene stearate, alkylphenol polyglycol ether and Pluronic ®.

Further auxiliaries which may be mentioned are those mentioned above.

Semi-solid preparations can be administered orally or cutaneously. They differ from the above-described suspensions and emulsions only by their higher viscosity.

For the preparation of solid preparations the active compound is mixed with suitable excipients, where appropriate with the addition of auxiliaries, and brought into the desired form.

Excipients which may be mentioned are all physiologically acceptable solid inert substances. Inorganic and organic substances serve all such. Inorganic substances are, for example, common salt, carbonates such as calcium carbonate, hydrogen carbonates, aluminum oxides, silicas, aluminas, precipitated or colloidal silicon dioxide and phosphates.

Organic substances are, for example, sugar, cellulose, foodstuffs and feedstuffs such as powdered milk, animal meals, cereal meals and shreds, and starches.

Auxiliaries are preservatives, antioxidants and colorants, which have already been listed above.

Further suitable auxiliaries are lubricants and glidants such as, for example, magnesium stearate, stearic acid, talc, bentonites, disintegrants such as starch or crosslinked polyvinylpyrrolidone, binders such as, for example, starch, gelatin or linear polyvinylpyrrolidone and also dry binders such as microcrystalline cellulose.

The active compounds can also be present encapsulated in the form of their abovementioned solid or liquid formulations.

The active compounds can also be administered in the form of an aerosol. For this, the active compound is finely divided in a suitable formulation under pressure.

It can also be advantageous to administer the active compounds in formulations which release the active compound in a delayed manner.

The administration of the active compounds preferably takes place together with the food and/or drinking water.

Single feedstuffs of vegetable origin such as hay, beets, cereals, cereal by-products, single feedstuffs of animal origin such as meat, fats, milk products, bonemeal, fish products, and furthermore single feedstuffs such as vitamins, proteins, amino acids, for example DL-methionine, and salts such as calcium carbonate and common salt count as food. Supplementary feedstuffs, ready-to-use feedstuffs and mixed feedstuffs also count as food. These containing single feedstuffs in a combination which guarantees balanced nutrition with respect to the energy and protein supply and also the supply of vitamins, mineral salts and trace elements.

The concentration of the active compounds in the food is normally about 0.01–500 ppm, preferably 0.1–50 ppm.

The active compounds can be added to the food as such or in the form of premixes or food concentrates.

Premixes and food concentrates are mixtures of the active compound with a suitable excipient.

The single feedstuffs or mixtures thereof count as excipients.

They can moreover contain further auxiliaries, such as, for example, substances which regulate the flow capability and miscibility, such as, for example, silicas, bentonites and lignin sulphonates. Moreover, antioxidants such as BHT or preservatives such as sorbic acid or calcium propionate can be added.

Concentrates for application via the drinking water must be formulated so that a clear solution or a stable homogeneous suspension results on mixing with the drinking water.

Suitable excipients are therefore water-soluble substances (food additives) such as sugar or salts (for example citrates, phosphates, common salt or sodium carbonate).

They can likewise contain antioxidants and preservatives.

The active compounds can be present alone in the formulations or mixed with other active compounds, mineral salts, trace elements, vitamins, proteins, colorants, fats or flavorings.

EXAMPLE A 15 4-week-old piglets from 2 litters each received 2 ml of a 0.25% strength aqueous solution, Δ0.6 mg of active compound per kg of body weight, of 2-(4-(4-(2-pyrimidinyl)-1-piperazinyl)-propyl)-1,2-benziso-thiazol3(2H)one 1,1-dioxide hydrochloride injected intramuscularly. The animals, grouped by litters beforehand, were brought together and observed for 2 hours. The animals fed together, and ranking fights did not occur.

EXAMPLE B

The experiment in Example A was repeated with 19 7-week-old piglets from 2 litters. The animals were injected intramuscularly with 2 ml of a 2% strength aqueous solution of 2-(4-(4-(2-pyrimidinly)-1-piperazinyl)-propyl)-1,2-benzisothiazol-3(2H)one 1,1-dioxide hydrochloride. The animals, grouped by litters beforehand, were brought together and observed for 2 hours. Ranking fights did not occur.

EXAMPLE C

The experiment in Example A was repeated with 10 7-week-old piglets, which were assembled from 4 litters. The animals received 2 ml of a 0.5% strength aqueous solution of ipsapirone hydrochloride (Δ0.7 mg per kg of body weight) injected intramuscularly before they were brought together. Ranking fights were not observed.

EXAMPLE 1

Preparation of 2-(4-(4-(2-pyrimidinyl)-1-piperazinyl)butyl)-1,2-benzoisothiazol-3(2H)one 1,1-dioxide

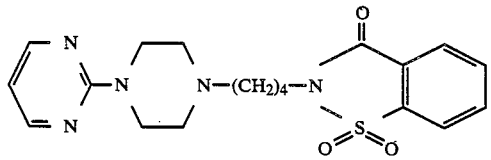

0.02 mol of 2-(4-bromobutyl)-1,2-benzoisothiazol-3-(2H)one 1,1-dioxide and 0.02 mol of 1-(2-pyrimidinyl) piperazine are stirred with 0.02 mol of $K_2CO_3$ in 150 ml of absolute dimethylformamide (DMF) for 1 hour at 100° C. The mixture is then concentrated. Water is added to the residue and the organic substance is taken up in methylene chloride ($CH_2CL_2$). The dried $CH_2CL_2$ phase is added to a silica gel column and eluted with $CH_2CL_2/CH_3OH$ (95:5).

Yield: 34% of theory; m.p.: 138°–139° C.

It will be appreciated that the instant specification and examples are set forth by way of illustration and not limitation, and that various modifications and changes may be made without departing from the spirit and scope of the present invention.

What is claimed is:

1. A method of suppressing ranking fights during assembly of groups of pigs which comprises administering to such pigs an amount effective therefor of a 2-pyrimidinyl-1-piperazine derivative of the formula (I)

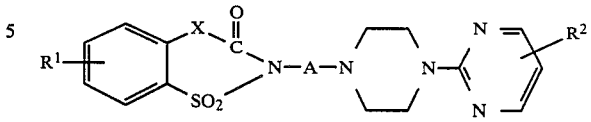

in which $R^1$ and $R^2$ each independently represents at least one radical selected from the groups consisting of hydrogen, $C_{1-4}$-alkyl, halogen, hydroxyl, nitro, $C_{2-4}$-alkenyl, $C_{1-4}$-alkoxy, $C_{1-4}$-alkylthio, $C_{1-4}$-halogenoalkyl, $C_{1-4}$-halogenoalkoxy and $C_{1-4}$-halogenoalkylmercapto, X is a direct bond or a radical

$R^3$ is hydrogen or $C_{1-4}$-alkyl, and

A is an optionally substituted alkylene radical with up to 6 C atoms, or a physiologically acceptable salt thereof.

2. A method according to claim 1, in which
$R^1$ is hydrogen, halogen, methyl, ethyl, methoxy, ethoxy, methylenedioxy or ethylenedioxy,
$R^2$ is hydrogen or halogen, and
A is an alkylene radical with 3 to 6 C atoms.

3. A method according to claim 1, in which
$R^1$ is hydrogen, chlorine, fluorine, methyl, ethyl, methoxy, ethoxy, methylenedioxy or ethylenedioxy,
$R^2$ is hydrogen, chlorine or fluorine,
$R^3$ is hydrogen, methyl or ethyl, and
A is n-propylene or n-butylene.

4. A method according to claim 3, in which
$R^1$ is hydrogen, fluorine, chlorine or methoxy, and
$R^2$ is hydrogen or fluorine.

5. A method according to claim 1, wherein the 2-pyrimidinyl-1-piperazine derivative is 2-(4-(4-(2-pyrimidinyl)-1-piperazinyl-propyl-1,2-benzisothiazol-3(2H)one-1,1-dioxide of the formula

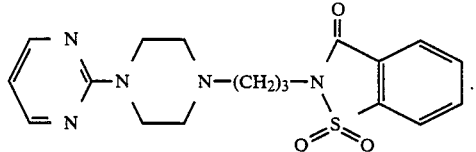

6. A method according to claim 1, wherein the 2-pyrimidinyl-1-piperazine derivative is 2-(4-(4-pyrimidinyl)-1-piperazinyl-1,2-benzisothiazol-3(2H)one-1,1-dioxide of the formula

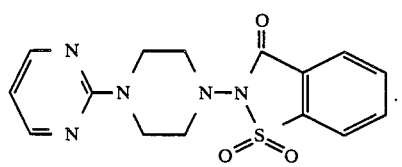

* * * * *